United States Patent
Tai et al.

(10) Patent No.: US 9,773,715 B2
(45) Date of Patent: Sep. 26, 2017

(54) MULTI-LAYER PACKAGING SCHEME FOR IMPLANT ELECTRONICS

(71) Applicant: California Institute of Technology, Pasadena, CA (US)

(72) Inventors: Yu-Chong Tai, Pasadena, CA (US); Han-Chieh Chang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/981,432

(22) Filed: Dec. 28, 2015

(65) Prior Publication Data

US 2016/0133540 A1 May 12, 2016

Related U.S. Application Data

(63) Continuation of application No. PCT/US2014/055379, filed on Sep. 12, 2014.
(Continued)

(51) Int. Cl.
*H01L 23/31* (2006.01)
*A61B 50/30* (2016.01)
*B81C 1/00* (2006.01)
*A61N 1/375* (2006.01)
*A61F 2/14* (2006.01)
(Continued)

(52) U.S. Cl.
CPC .......... *H01L 23/3135* (2013.01); *A61B 50/30* (2016.02); *A61F 2/14* (2013.01); *A61N 1/36046* (2013.01); *A61N 1/3758* (2013.01); *B81C 1/00* (2013.01); *H01L 21/56* (2013.01);
(Continued)

(58) Field of Classification Search
CPC ........................... H01L 23/3135; H01L 21/56
See application file for complete search history.

(56) References Cited

U.S. PATENT DOCUMENTS

| 2002/0187260 A1 | 12/2002 | Sheppard, Jr. et al. |
| 2005/0249901 A1* | 11/2005 | Yializis ............... B32B 7/02 |
| | | 428/35.7 |

(Continued)

FOREIGN PATENT DOCUMENTS

| EP | 1680803 B1 | 7/2006 |
| WO | 2012174300 | 12/2012 |
| WO | 2015041944 A1 | 3/2015 |

OTHER PUBLICATIONS

International Application No. PCT/US2014/55379, International Search Report and Written Opinion dated Nov. 24, 2014, 18 pages.
(Continued)

*Primary Examiner* — Dung Le
(74) *Attorney, Agent, or Firm* — Kilpatrick Townsend & Stockton LLP

(57) ABSTRACT

The present invention provides a micropackaged device comprising: a substrate for securing a device with a corrosion barrier affixed to the substrate, wherein the corrosion barrier comprises a first thin-film layer, a metal film coating the thin-film layer and a second thin-film layer to provide a sandwich layer; and optionally at least one feedthrough disposed in the substrate to permit at least one input and or at least one output line into the micropackaged device, wherein the micropackaged device is encapsulated by the corrosion barrier. Methods of producing the micropackaged device are also disclosed.

14 Claims, 9 Drawing Sheets

Related U.S. Application Data

(60) Provisional application No. 61/878,983, filed on Sep. 17, 2013.

(51) Int. Cl.
　　*A61N 1/36*　　　(2006.01)
　　*H01L 21/56*　　　(2006.01)
　　*H01L 23/00*　　　(2006.01)
　　*A61N 1/372*　　　(2006.01)

(52) U.S. Cl.
　　CPC ......... *A61N 1/37211* (2013.01); *H01L 23/564* (2013.01); *H01L 2924/0002* (2013.01)

(56) References Cited

U.S. PATENT DOCUMENTS

| | | | |
|---|---|---|---|
| 2007/0216300 A1* | 9/2007 | Lee | B05D 1/60 313/512 |
| 2008/0051848 A1 | 2/2008 | Greenberg et al. | |
| 2010/0148345 A1 | 6/2010 | Eckhardt et al. | |
| 2010/0262208 A1 | 10/2010 | Parker | |
| 2010/0265680 A1 | 10/2010 | Tai et al. | |
| 2010/0294024 A1* | 11/2010 | Kumar | B82Y 20/00 73/38 |
| 2011/0132449 A1 | 6/2011 | Ramadas et al. | |
| 2013/0184593 A1 | 7/2013 | Tepper et al. | |

OTHER PUBLICATIONS

Chang, et al., "Adhesion-enhancing surface treatments for parylene deposition", IEEE, 16th International Solid-State Sensors, Actuators and Microsystems Conference, Jun. 5-9, 2011, pp. 390-393.

Chang, et al., "High density 256—channel chip integration with flexible parylene pocket", IEEE, 16th International Solid-State Sensors, Actuators and Microsystems Conference, Jun. 5-9, 2011, pp. 378-381.

Chang, et al., "High yield packaging for high-density multi-channel chip integration on flexible parylene substrate", IEEE 25th International Conference on, Micro Electro Mechanical Systems, Jan. 29-Feb. 2, 2012, pp. 353-356.

Hu, et al., "Measurement of Water Vapor Transmission Rate in Highly Permeable Films", Journal of Applied Polymer Science, vol. 81, Issue 7, Aug. 15, 2001, pp. 1624-1633.

Huang, et al., "Parylene-Pocket Chip Integration", IEEE 22nd International Conference on, Micro Electro Mechanical Systems, Jan. 25-29, 2009, pp. 749-752.

Li, et al., "Corrosion Behavior of Parylene-Metal-Parylene Thin Films in Saline", ECS Transactions, vol. 11, Issue 18, 2008, pp. 1-6.

Mojarradi, et al., "A Miniaturized Neuroprosthesis Suitable for Implantation Into the Brain", IEEE Transactions on Neural Systems and Rehabilitation Engineering, vol. 11, Issue 1, Mar. 2003, pp. 38-42.

Pang, et al., "A New Multi-Site Probe Array with Monolithically Integrated Parylene Flexible Cable for Neural Prostheses", IEEE Engineering in Medicine and Biology 27th Annual Conference,, Sep. 1-4, 2005, pp. 7114-7117.

PCT/US2014/055379, "International Preliminary Report on Patentability", dated Mar. 31, 2016, 10 pages.

Sawano, et al., "Sealing method of PDMS as elastic material for MEMS", Proceedings on Micro Electro Mechanical Systems, Jan. 13-17, 2008, pp. 419-422.

CN201480043546.3 , "Office Action", dated May 18, 2017, 4 pages.

EP14846305.2 , "Extended European Search Report", dated Mar. 28, 2017, 7 pages.

* cited by examiner

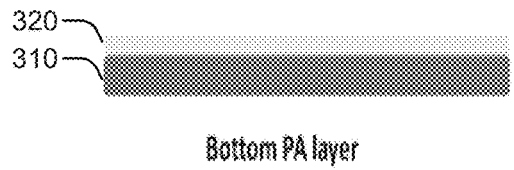
Bottom PA layer
FIG. 3A
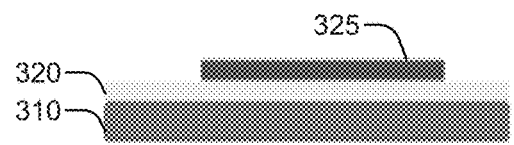
Sacrificial PR layer
FIG. 3B
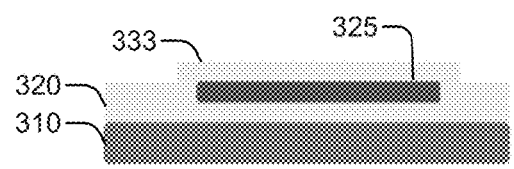
1st PA layer
FIG. 3C
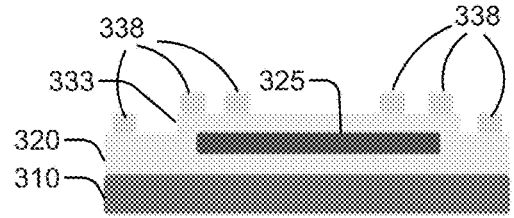
Metal lift-off
FIG. 3D
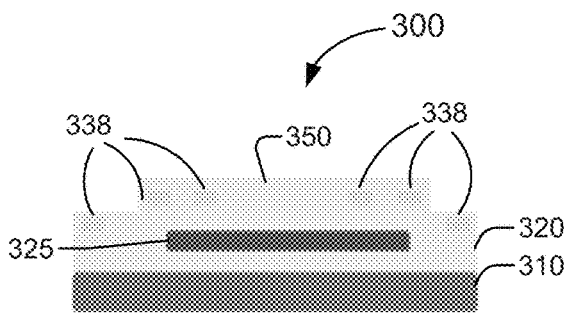
2nd PA layer
FIG. 3E
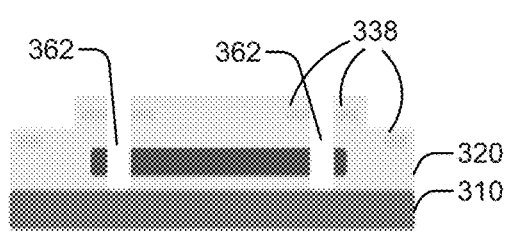
Plasma etch
FIG. 3F
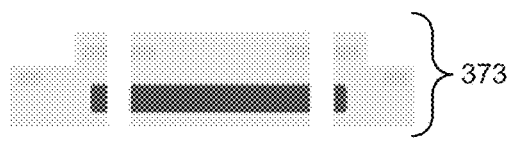
Device release
FIG. 3G

FIG. 4A
FIG. 4B
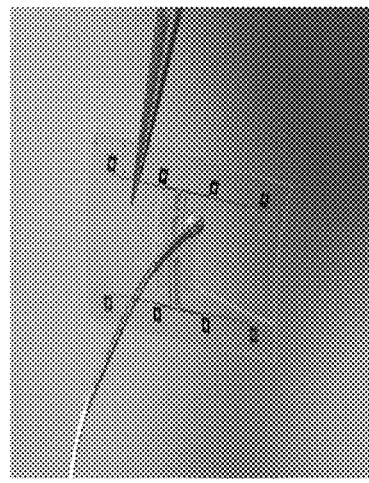 
FIG. 5A
FIG. 5B
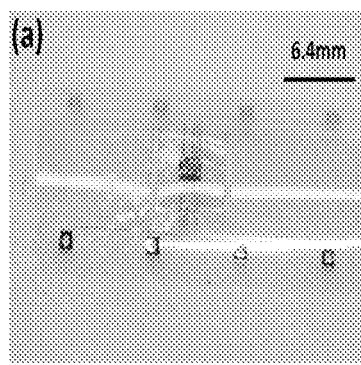 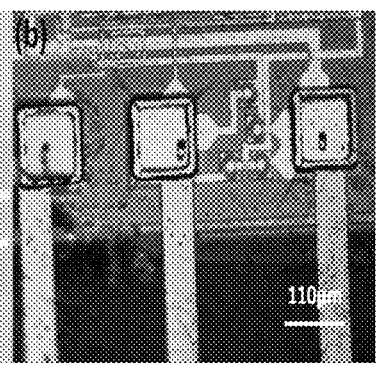
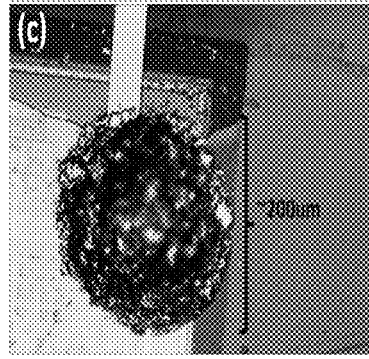 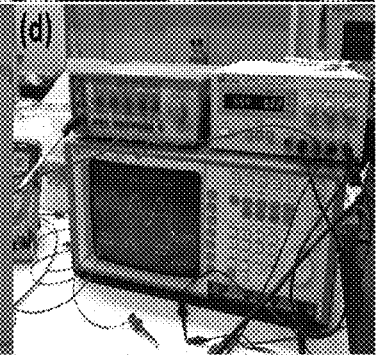
FIG. 5C
FIG. 5D

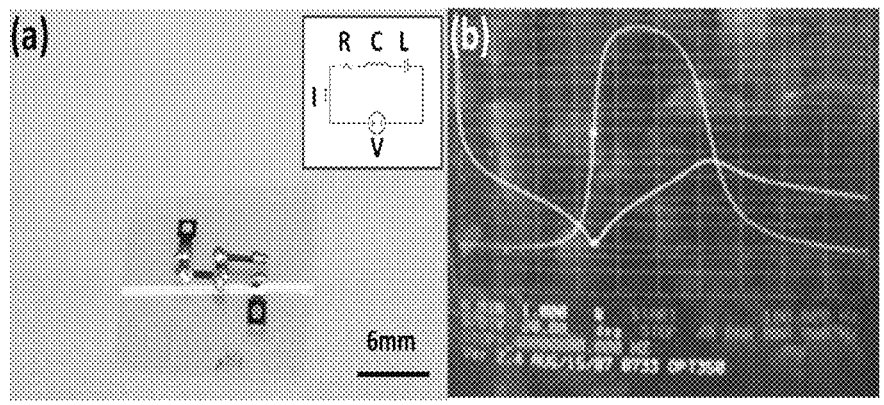
FIG. 6A    FIG. 6B
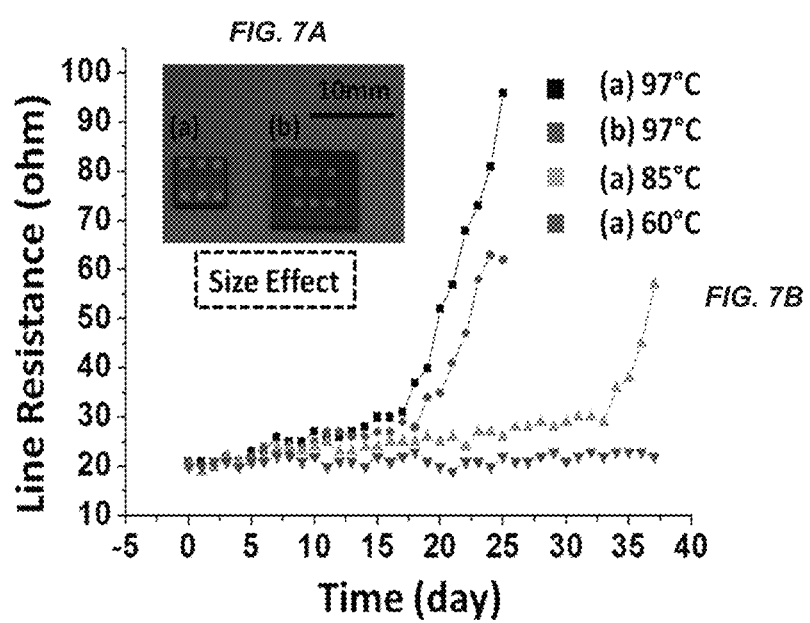
FIG. 7A
FIG. 7B

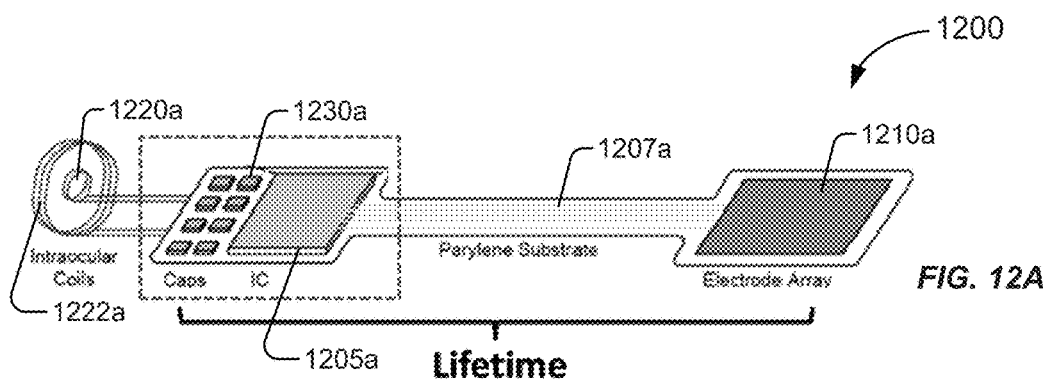
*FIG. 12A*
Retinal IC chip is operated at ~mA
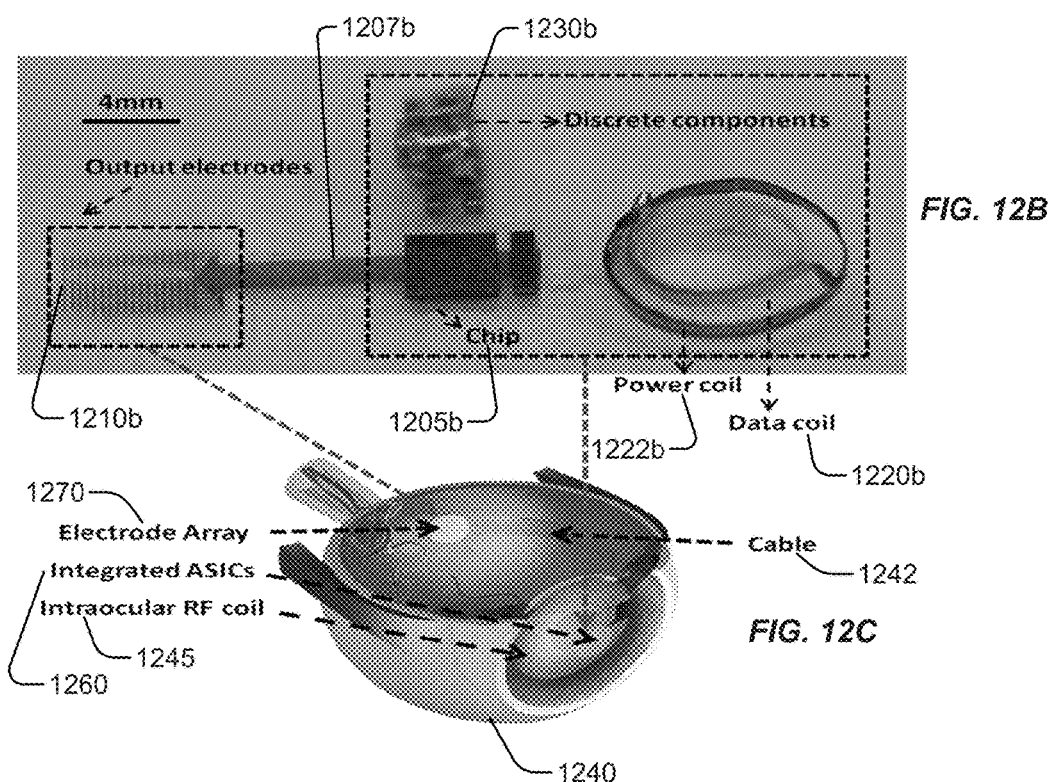
*FIG. 12B*
*FIG. 12C*

MULTI-LAYER PACKAGING SCHEME FOR IMPLANT ELECTRONICS

CROSS-REFERENCES TO RELATED APPLICATIONS

The present application is a continuation of PCT/US2014/055379, filed Sep. 12, 2014, which application claims priority to U.S. Provisional Application No. 61/878,983, filed Sep. 17, 2013, the contents of which is hereby incorporated by reference in its entirety for all purposes.

STATEMENT REGARDING FEDERALLY SPONSORED RESEARCH OR DEVELOPMENT

This invention was made with government support under Grant No. EEC0310723 awarded by the National Science Foundation. The government has certain rights in the invention.

BACKGROUND OF THE INVENTION

MEMS technology has been used more and more in biomedical applications for neural prosthetic implantation (see, M. M. Mojarradi et al., *IEEE Transactions on Neural Systems and Rehabilitation Engineering*, vol. 11, pp. 38-42 (2003); C. Pang et al. "A new multi-site probe array with monolithically integrated parylene flexible cable for neural prostheses" in Digest Tech. Papers EMBS '05 Conference, Jan. 12-18, 2006, pp. 7114-7117). These devices, however, will have to endure harsh and corrosive body fluids (see, W. Li et al., *ECS Transactions*, vol. 11, pp. 1-6 (2008)). Therefore, biostable and hermetic-like packaging is needed to protect the implant.

One of the biggest challenges that a prosthetic implant has to overcome is the reliable packaging of integrated circuit (IC) chips so that bio-devices can withstand corrosive body fluids. What is needed in the art is a complete wireless retinal implant with high density multi-channel IC chips, discrete components (caps, inductors, and oscillators), and coils (power and data coils) packaged with a high-density stimulating electrode array. Appropriate packaging of the retinal implant in a mammalian body to achieve a long lifetime is also needed. The present invention satisfies these and other needs.

BRIEF SUMMARY OF THE INVENTION

The present invention provides a new protection scheme of a thin-film-(metal)-thin-film sandwich architecture for a corrosion barrier. The sandwich architecture is a flexible composite. Advantageously, the corrosion barrier has a low water vapor transmission rate (WVTR) and preserves flexibility, which are important features for devices such as retinal implants.

As such, in one embodiment, the present invention provides an encapsulated micropackaged device, the micropackaged device comprising:
 a substrate for securing a device;
 a corrosion barrier affixed to the substrate, wherein the corrosion barrier comprises a first thin-film layer, a metal film coating the first thin-film layer and a second thin-film layer to provide a sandwich layer; and optionally at least one feedthrough disposed in the substrate to permit at least one input and or at least one output line into the micropackaged device, wherein the micropackaged device is encapsulated by the corrosion barrier.

In another embodiment, the present invention provides a method for preparing a micropackaged device, the method comprising:
 providing a substrate for securing the device;
 coating the device with a first thin-film layer to provide a first thin-film layer over the device;
 depositing a surrounding metal film over the first thin-film layer to produce a metal coat; and
 coating the metal coat layer with a second thin-film layer to provide an encapsulated micropackaged device.

In certain aspects, the present invention provides a micropackaging architecture using a parylene-metal-parylene flexible composite. The packaging is suitable for both active and passive components, including amplifier chips, discrete components, and conduction chips. In certain instances, the micropackaging architecture is especially designed to integrate a small amplifier chip. Advantageously, the micropackaging architecture enhances the lifetime of the micropackaged components.

These and other aspects, objects and advantages will become more apparent when read with the detailed description and figures which follow.

BRIEF DESCRIPTION OF THE DRAWINGS

FIGS. 3 A-G show one embodiment of a fabrication process of a substrate structure of the present invention; (A) shows a parylene-C layer on a silicon substrate; (B) shows photoresist being used as a sacrificial layer; (C) shows a first parylene deposition; (D) shows metal deposition and lift-off; (D) shows a second parylene deposition; (E) shows a plasma etching step; and (G) shows the silicon wafer is released.

FIGS. 4 A-B (A) shows a parylene pocket opened by a spatula after releasing the sacrificial photoresist; (B) with wafer dicing tape as a fixation substrate, the pocket becomes easier to open.

FIGS. 5 A-D (A) shows a chip is inserted and aligned; conductive epoxy is applied to make connection; (B) shows alignment accuracy of 10 µm can be achieved; (C) shows the size of conductive epoxy drop is 200 µm in diameter; and (D) shows that signal is monitored by an oscilloscope.

FIGS. 6 A-B (A) shows the topside of the series RLC circuit built by discrete components; (B) shows that resonant frequency is measured by an impedance analyzer.

FIGS. 7 A-B (A) shows the size difference of the chips being compared; (B) shows line resistance vs time of samples coated by 40 µm parylene-C only soaked in high temperature saline solution.

FIGS. 12 A-C (A-B) show a schematic representation of the retinal implant connected with IC chips, coils, and discrete components; (C) shows implantation into a mammalian eye.

DETAILED DESCRIPTION OF THE INVENTION

I. Embodiments

Aspects of the present invention are directed to a micropackaged electronic device(s) and/or component(s) for use as well as methods of making the micropackaged device for an implantable medical device. In some aspects, the electronics are hermetically sealed within a biocompatible housing.

Figure 1:
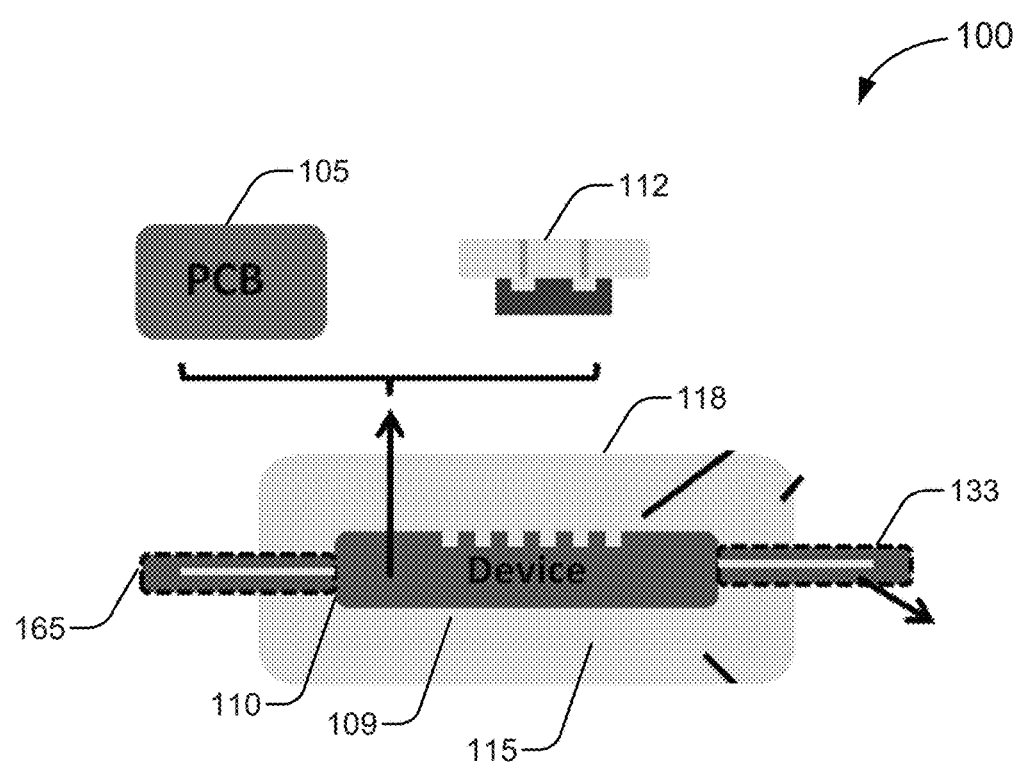
FIG. 1 shows one embodiment of a micropackaged device of the present invention.

FIG. 1 illustrates one embodiment of the micropackaged device 100 of the present invention. In certain aspects, the micropackaged device 100 comprises a substrate for securing a device 110. A wide variety of devices can be packaged according to the present invention. Suitable devices include, but are not limited to, an integrated circuit (IC) chip, a printed circuit board (PCB), a microelectromechanical system (MEMS), a capacitor, an inductor, an oscillator, or a combination thereof. The devices to be protected can be a wired or a wireless PCB, thin-film integrated device, and the like. If the component or device is wireless (e.g., with a coil), the entire device can be totally encapsulated in the enclosure. Small electronic components can be mounted on a printed circuit board, which minimizes the amount of space necessary for the implant. In one embodiment, FIG. 1 shows the device comprising a combination of a PCB 105 and a thin-film integrated device 112. The components can be both passive and active components. Those of skill in the art will recognize that a variety of components can be used.

The micropackaged device 100 comprises a corrosion barrier or sandwich layers having at least 3 components. The corrosion barrier is made from coating the device with a first thin-film layer 109 to provide a first thin-film layer over the device. The first thin-film layer is made of a material selected from the group of parylene, polyimide, Teflon or Kapton. In a preferred embodiment, the first thin-film layer is parylene.

As shown in FIG. 1, after the first thin-film layer 109 is layered over the device, a surrounding metal film 115 is deposited over the first thin-film layer 109 to produce a metal coat. The metal film 115 is a biocompatible metal. The metal film 115 is selected from the group of Au, Ag, Pt, Pd, Ti and alloys. Preferrably the metal layer is Au, Ag or Pt.

The micropackaged device comprises a second thin-film layer 118 over the metal coat 115. Preferably, the layer 118 over the metal coat 115 is a second thin-film layer. The second thin-film layer 118 is made of a material selected from parylene, polyimide, Teflon and Kapton. Preferrably, the second thin-film layer is made of parylene.

In certain aspects, the present invention provides a micropackaged device, which is an encapsulated micropackaged device. In a preferred aspect, the corrosion barrier has a parylene-metal-parylene sandwitch architecture. The corrosion barrier is both reliable (long lived) and flexible.

The substrate can have any number of designs including recesses and/or pockets for mounting electronic components and devices. As the number of devices and components will vary, so too will the number of recesses and pockets, each of which can have a different dimension. In some embodiments of the present invention, there may be an inner filler material to protect components and to provide impact strength.

In certain aspects, the corrosion barrier or each of the sandwitch layers is optionally affixed to the substrate with an adhesive. For example, the adhesive can be a low permeation adhesive. Suitable adhesives include, but are not limited to, epoxy, silicone, polyimide or a combination thereof.

In certain embodiments, the micropackaged device 100 of the present invention comprises optionally at least one feedthrough 133, 165 (shown as dashed lines to indicate that they are optional) disposed in the substrate to permit at least one input and/or at least one output line into the encapsulated micropackaged device. For example, if the device is wired, a cable can exit the encapsulation to make an external connection. The substrate can be integrated into the device or can be a separate component.

In certain aspects, the micropackage optionally contains at least one hermetic feedthrough 133 or 165 disposed in either the substrate, or bottom of the micropackage housing. In the embodiment shown in FIG. 1, two elongate hermetic feedthroughs 133, 165 are disposed in apertures of the micropackage 100. Such feedthroughs 133, 165 are each configured to permit an input/output line to infiltrate the hermetic enclosure or housing without degrading the hermeticity of the enclosure. Input/output lines may be, for example, wires (metal, copper, fiber optic, and the like), cables, tubes, and the like that facilitate the transfer of energy, data, or power between functional components and other implantable devices, external components, and the like.

In certain aspects, the feedthroughs enable the production of thinner or more compact implantable components as the device can be spread over larger surface areas. A "feedthrough" can include an electrically conductive path extending through an insulator (or insulative member). In some embodiments, the electrically conductive path electrically connects the functional components located in the interior of the encapsulated housing or sealed enclosure (i.e., a hermetically sealed, housing, and the like) of the micropackage to functional components external to the hermetic enclosure. That is, in some embodiments, the conductor provides an electrically conductive path from one side of the insulator in the enclosure to another side of the insulator outside the enclosure.

In certain aspects, the corrosion barrier has at least one parylene-metal-parylene sandwitch althouth multiple sandwitch layers can be used. Parylene-C is one preferred parylene material, although other parylenes such as parylene N, C, D, HT, AM, A or combinations thereof can also be used. A skilled artisan will appreciate that the first and second thin-film layers can comprise other materials as well. In one aspect, the corrosion barrier e.g., parylene-metal-parylene archetecture creates an enclosed housing hermetically sealing the device and/or substrate.

In one aspect, the corrosion barrier is coextensive with the entirety of the interior of the enclosed housing. Alternatively, the corrosion barrier is coextensive with about 10% to about 90% such as 20% to about 60% or even about 50% of the total area of the interior of enclosed housing or an area commensurate with the device. In other aspects, the corrosion barrier is coextensive with about 5, 10, 20, 30, 40, 50, 60, 70, 80, 90 or about 99% of the interior area of the enclosed housing.

In one aspect, the corrosion barrier protects a metal pad(s) or the electronics of the device. The corrosion barrier can be attached to a device by an adhesive with an adhesion promoter.

In certain aspects, the micropackaged device of the present invention is an implantable prosthesis, such as a totally implantable prosthesis that can be temporarily or permanently implanted into a mammal such as a human being. The enclosure can be hermetically sealed to secure against the entry of water, water vapor and foreign bodies in order to maintain the proper functioning and reliability of the contents therein.

Communication with such an implanted prosthesis can be performed using either percutaneous connectors or wireless communication methods. An advantage of a wireless communication method over a percutaneous connector is the elimination of issues relating to possible infection or irritation related to devices that perforate the skin. Some of the kinds of signals that are communicated between an implanted prosthesis and an external device include power signals and data signals. Power signals can include signals that provide power from an external power supply to an implanted prosthesis, so that for example, a battery or electronic device present in the implanted prosthesis can be maintained in a suitable state of charge, or so that for example, a battery can be eliminated from the implanted prosthesis.

In one aspect of the present invention, there is provided a protective packaging for a long lifetime for a retinal implant in a mammalian subject such as a human being. In certain aspects, the use of an encapsulating coating together with a corrosion barrier is used to protect the implant device.

In another embodiment, the present invention provides a method for preparing a micropackaged device, the method comprising:
providing a substrate for securing the device;
coating the device with a first thin-film layer to provide a first thin-film layer over the device;
depositing a surrounding metal film over the first thin-film layer to produce a metal coat; and
coating the metal coat layer with a second thin-film layer to provide an encapsulated micropackaged device.

In certain aspects of the method, the first thin-film layer is made of a material selected from the group of parylene, polyimide, Teflon and Kapton. After the first thin-film layer is coated on the device, a metal layer, such as a biocompatible metal, is deposited onto the first film-layer. In order to accomplish the deposition of metal, a holder is used to deposit the metal in a plurality of stages. In certain instances, the methods provide depositing a surrounding metal film over the first thin-film layer to produce a metal coat in a plurality of stages. For example, in a first stage, the device is held at about 45° to the metal deposition source to complete encapsulation of one side of the device. In certain aspects, in a second stage, the device is flipped 180 ° and held at about 45° to the metal deposition source to complete encapsulation of the other side of the device.

Figure 2A:
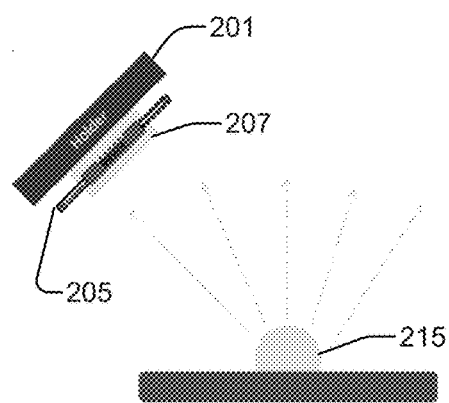
FIGS. 2A-D show (A) a device being held at an angle before metal deposition; (B) a device being held at an angle during metal deposition; (C) shows a device being held at an angle after being flipped before metal deposition; and (D) shows a device being held at an angle after being flipped during metal deposition.
Figure 2B:
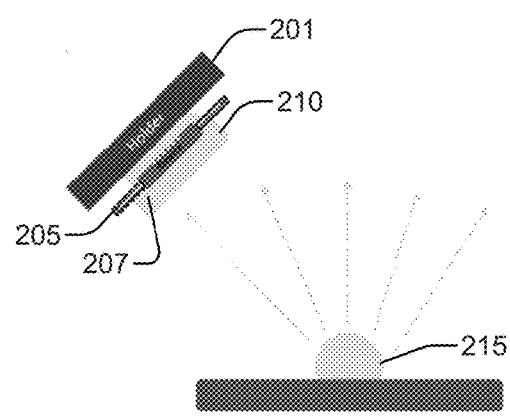

Turning to FIG. 2A, in certain aspects, the first thin-film layer coating 207 (e.g., parylene) is done on the device to be protected, and then the device 205 is fixed on a holder or clamp 201 at about 45° to the metal source, although the exact angle is not critical as long a metal deposition from the metal source 215 is efficient. As shown in FIG. 2B, the metal 210 is layered onto the first thin-film layer 207.

Figure 2C:
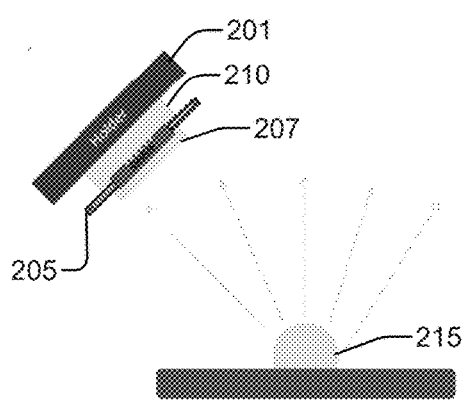
Figure 2D:
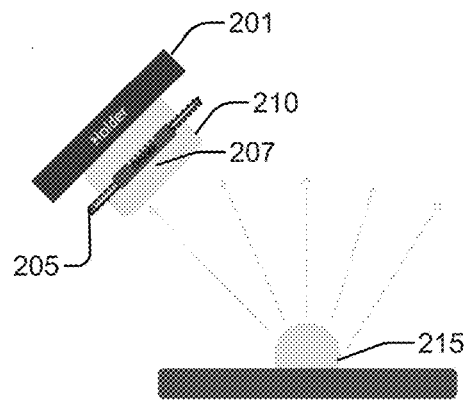

Next, as is shown in FIG. 2C, the device 205 is flipped up-side-down (180°) to expose the first layer 207 that was not coated with metal. Again, as shown in FIG. 2D, metal is deposited to create a continuous metal film and ensure total encapsulation of the device.

In certain aspects, the holder itself is rotated such as continually rotated to create a uniform metal film. The encapsulated device is then removed from the holder, and the second layer (e.g., parylene) is coated to encapsulate the metal layer to finish this sandwich structure (e.g., parylene-metal-parylene) packaging scheme.

In certain preferred aspects, the depositing a surrounding metal film is performed with a holder or clamp in constant motion. The first thin-film layer, the metal film coating and the second thin-film layer create a sandwich corrosion barrier. In certain preferred aspects, the sandwich is at least one parylene-metal film-parylene sandwich architecture. In certain aspects, the present invention provides the micropackaged device produced by the foregoing methods.

In one aspect, the foregoing methods of micropackaging are done in a high throughput or mass production fashion. Using robotics and computer implemented methods of the foregoing, the micropackaged device is mass produced.

In order to test the sandwich architecture, commercially available amplifier bare dies (AD8042), with die size (mils) 45×65, were packaged and tested. In order to handle and integrate the small bare dies, a parylene pocket (see, R. Huang, Y. C. Tai, "Parylene pocket chip integration", in Digest Tech. Papers MEMS '09 Conference, Sorrento, Italy, Jan. 25-29, 2009, pp. 749-752) structure on parylene substrate was designed and fabricated as shown in FIG. 3A-G.

In certain aspects, the present invention provides a fabrication process 300 for a parylene-substrate, such as a flexible parylene-C substrate. In one exemplary embodiment, FIG. 3A shows a 5 µm first parylene-C layer (bottom layer) 320 deposited on a silicon wafer substrate 310 such as a HMDS treated silicon wafer, which aids in the device being detached such as being released in distilled or deionized water, preferably released in deionized water.

Next, as is shown in FIG. 3B, adjacent to the first parylene layer 320 (bottom parylene layer) is a sacrificial photoresist 325 of about 1 µm is coated on the bottom parylene-C and patterned by a photo-lithography process to create a sacrificial area to accommodate the bare dies. In certain embodiments, the sacrificial layer is about 0.5 to about 2 µm thick such as about 1 µm thick or about 0.9 to about 1.5 µm in thickness. Suitable materials for the photoresist layer include, but are not limited to, SU-8, AZ4620, AZ1518, AZ4400, AZ9260, THB-126N, WPR-5100, BCB, polyimide, or a combination thereof.

After cleaning with dilute hydrofluoric acid, another parylene layer 333 is applied. The parylene layer is about 5 µm thick and is deposited to encapsulate the sacrificial layer 325 and serves as the base layer for metal deposition. The parylene layer can be about 1, 2, 3, 4, 5, 6, 7, 8, 9 or 10 µm thick.

As is shown in FIG. 3D, a metal combination 338 (e.g., Ti/Au 0.02/0.3 µm) is then patterned on the parylene-C layer by a lift-off process for electrical connection by e-beam evaporation. In certain aspects, the metal 338 used for the lift-off is a titanium/gold (Ti/Au) alloy. However, other suitable metals and alloys include, but are not limited to, Cr/Au, Ni/Au, Ti/Au, Al/Ti, Ag/Ti, Cr/Au/Ti/Ni/Au, Ni/Pd/Au, Ti/Ni/Au or combinations thereof. Those of skill in the art will know of other metals useful for the present invention. The metal layer 333 provides an electrical connection.

A second parylene layer 350 (top layer) such as a parylene-C (about 5 µm) layer is then deposited to complete the sandwich structure. The top layer can be about 1, 2, 3, 4, 5, 6, 7, 8, 9 or 10 µm thick.

As is shown in FIG. 3F, electrodes and device outlines 362 are opened by oxygen plasma to finish the fabrication. FIG. 3G shows the device 373 after being released from the substrate.

The foregoing pocket structure was designed to handle a small amplifier chip, which is dimensioned at about 1 mm by 1.5 mm. The sacrificial photoresist layer can be dissolved in acetone to create a space for the small amplifier chip, which can be aligned align under a microscope. A spatula can be used to open the pocket and the discrete component can be inserted. Those of skill in the art will recognize that the pocket can be dimensioned to suit the components to be packaged.

The pocket created by the process 300 can be opened by a spatula after releasing the sacrificial photoresist, as shown in FIG. 4A-B. Wafer dicing tape can be applied to temporarily fix the pocket device so the pocket can be opened from the bottom substrate. After the chips (or other electronic components) are inserted into the pocket, the metal pads on the chip are then aligned with the metal bonding pads on the pocket structure under microscope. An alignment accuracy of around 10 µm can be achieved, which is adequate for bonding pads with a size of 110 µm×1-10 µm.

In certain aspects, the packaging sandwich architecture hosts electronic components such as application specific integrated circuits (ASICs), which are interconnected via metallization traces. In one embodiment, the fabricated flexible parylene-C substrate is connected with an IC chip and other discrete components. In certain other aspects, the substrate or micro-module of the present invention contains a variety of components including, but not limited to, one or more integrated circuits, ASICs, interconnect layers, heat sinks, conductive vias, passive devices, MEMS devices, sensors, pre-manufactured electrical components, transistors, resistors, capacitors, inductors, micropumps and filters. The components are arranged and stacked within the module in a wide variety of different ways. The layers and components of the module can be deposited and processed using various conventional wafer level processing techniques, such as spin coating, lithography and/or electroplating.

Turning now to FIG. 5A, conductive epoxy adhesive (MG Chemicals) is used and manually applied on top of the pads individually using needles to make the electrical and mechanical connection. In order to measure a signal, five small bonding pads can be used and connected as well. Wires are connected to the pre-designed through holes on metal layers by conductive epoxy for external functional testing. A power supply and function generator are then connected to the pocket devices and "active" signal can be constantly monitored using an oscilloscope (HP 54503A). FIG. 5A shows a chip being inserted and aligned; conductive epoxy is then applied to make connection. FIG. 5B shows alignment accuracy of 10 µm can be achieved. FIG. 5C shows the size of conductive epoxy drop is about 200 µm in diameter. FIG. 5D shows that the signal is monitored by oscilloscope.

The mean time to failure (MTTF) of this system is defined as the time when the signal is lost.

Discrete components, such as resistors, inductors, and capacitors, are also packaged to build a series RLC circuit. Because the size and bonding pads of the discrete components are much bigger than amplifier bare dies, no pocket structures are needed for this integration. The fabrication process of this device and integration of this system has been disclosed (see, J. H. Chang, D. Kang, Y. C. Tai, "High yield packaging for high-density multi-channel chip integration on flexible parylene substrate", in Digest Tech. Papers MEMS '12 Conference, Paris, Jan. 29-Feb. 2, 2012, pp. 353-356).

Turning now to FIG. 6A, the topside of the series RLC circuit built by discrete components is shown. FIG. 6B shows the resonant frequency measured by an impedance analyzer. The measurement result with the following parameters: resistance is negligible; capacitance is 0.91 µF; inductance is 100 pH.

The resonant frequency can be calculated by the following equation:

$$w = 2\pi f = \frac{1}{\sqrt{L \times C}} \qquad (1)$$

The measurement result of resonant frequency as a functional indicator with the impedance analyzer is around 13.7 MHz, while the theoretical resonant frequency is calculated to be 16.684 MHz. The connecting wires and conductive epoxy contributes to the offset. The mean time to failure (MTTF) of this system is defined as the time when the resonant frequency cannot be measured anymore.

Dummy conduction chips with different sizes are designed to compare the "size effect" on lifetime, as shown in FIG. 7 A-B. The fabrication process of the parylene device and the integration are the same as those for discrete components.

Figure 8:
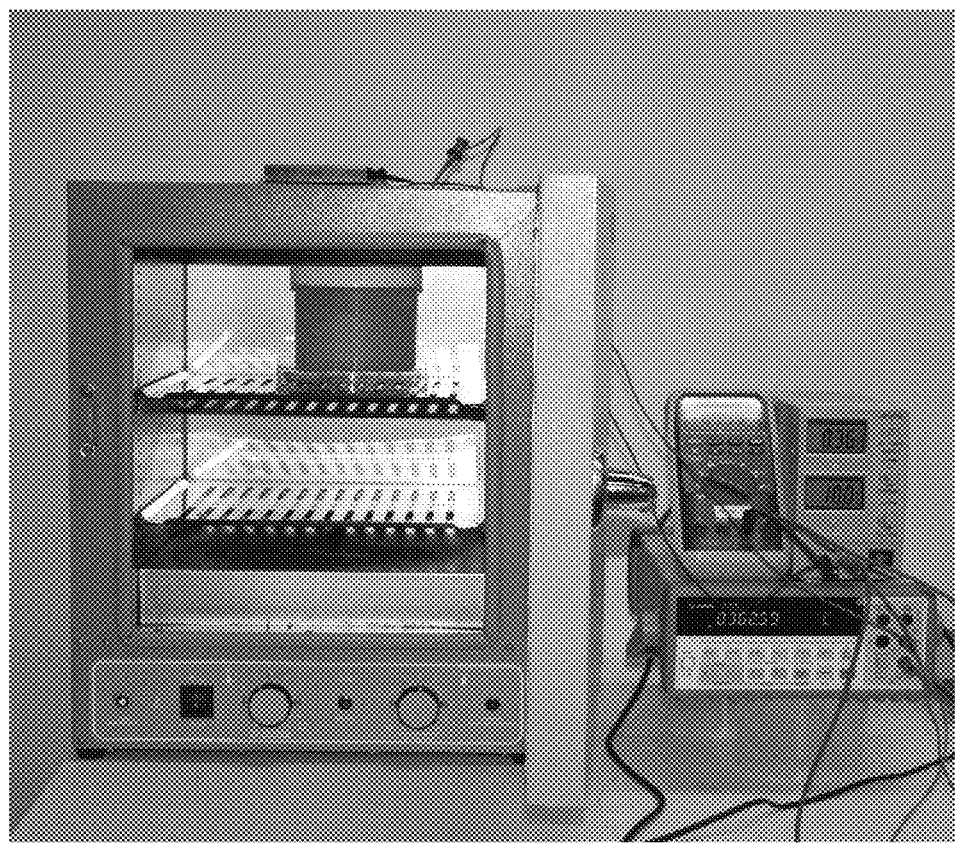
FIG. 8 shows a measurement setup for the active soaking test for a dummy conduction chip. Power supply, multimeter, and dummy conduction chip soaked in saline are arranged in series. Door is opened to show the setup inside.

FIG. 8 shows the measurement setup of active soaking test for dummy conduction chip. Power supply, multi-meter, and dummy conduction chip soaked in saline are arranged in series. The current is continuously sent in and the change of the current is constantly monitored by multi-meter to calculate the changes of resistance. The MTTF of this system is defined as the time when 50% change in the line resistance happens.

II. Examples

Example 1 Shows the Flexibility of the Sandwich Corrosion Barrier

Figures 9A, 9B:
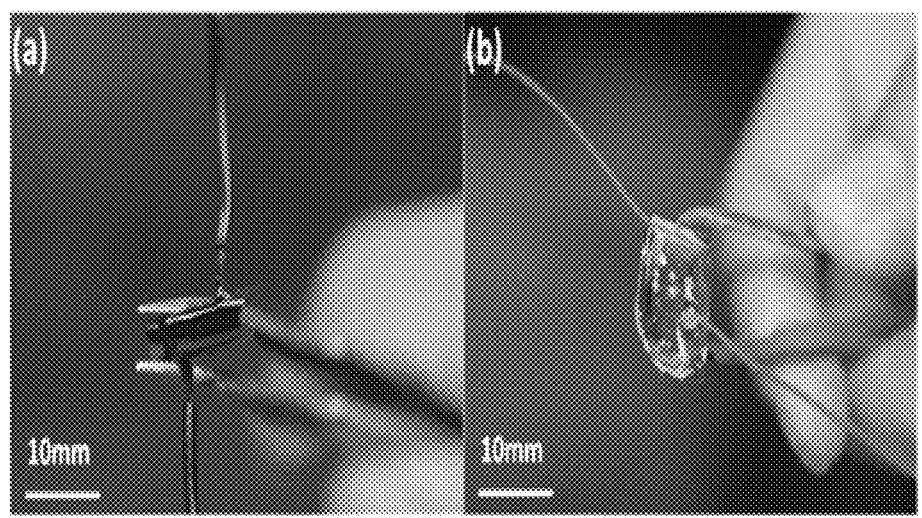
FIGS. 9 A-B (A) shows after sandwich layer protection, the device is still highly flexible; (B) shows the device becomes inflexible after coating with thick silicone; thickness needs to be more than 5 mm.
Figure 10A:
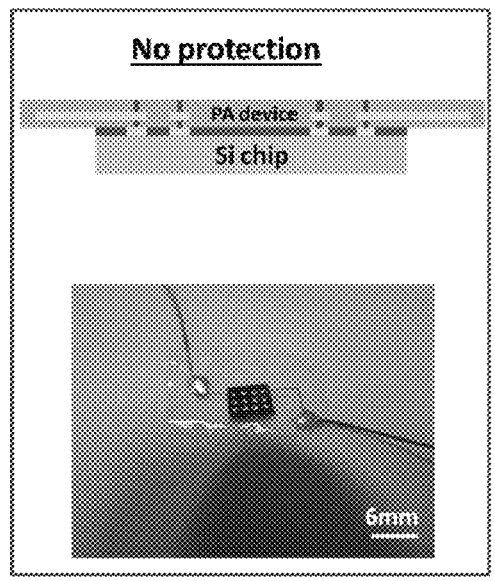
FIGS. 10 A-D show 4 devices being compared. (A) shows no protection was used; (B) shows a 40 μm parylene-C layer was used as protection; (C) shows a parylene-C coated bio-compatible silicone; and (D) shows an inventive parylene-C-metal-parylene C architecture.
Figure 10B:
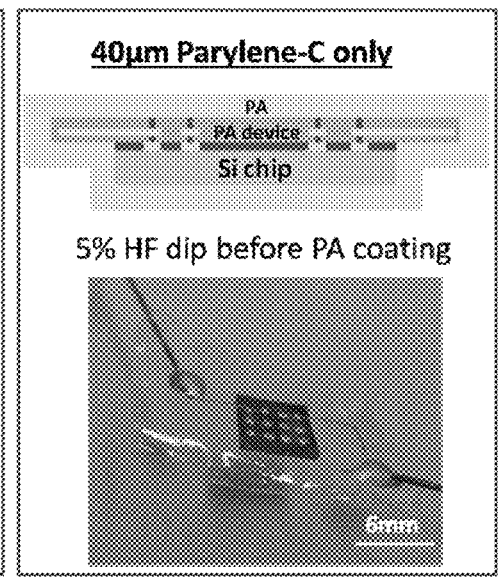
Figure 10C:
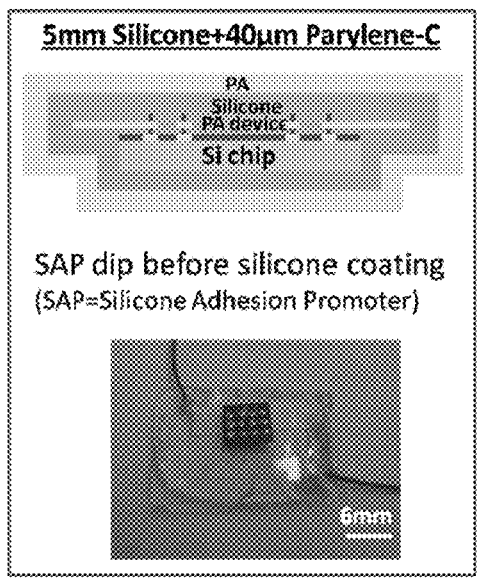
Figure 10D:
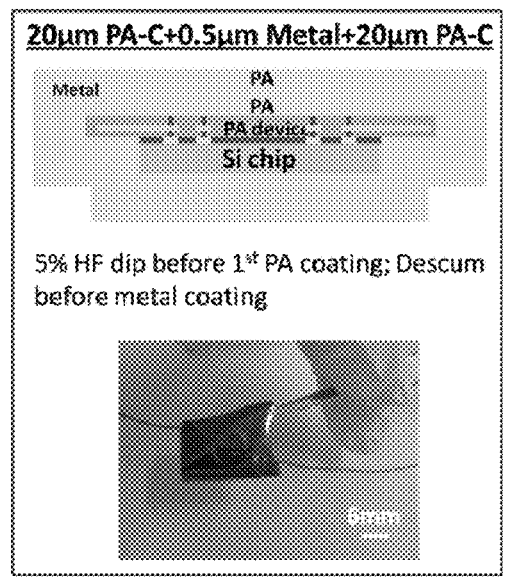

Water vapor permeation is one of the main causes of failure in parylene devices when implanted. In order to create better protection, bio-compatible metals, such as titanium, gold, platinum and combinations thereof are chosen as the metals in parylene-metal-parylene flexible composite protection layers to protect devices from water vapor corrosion. FIG. 9A shows that even after sandwich layer protection, the device is highly flexible. FIG. 9B shows that the device becomes inflexible after coating with thick silicone.

Example 2 Shows a Comparison of Various Protection Schemes Using MTTF

Water vapor transmission rates (WVTR) of a 0.5 µm metal with high flexibility is lower than that of a 5 mm-thick silicone by a theoretical calculation. Advantageously, the device of the present invention is highly flexible even after sandwich layer protection. However, extra care needs to be taken of the metal coating. Samples need to be fixed at around 45° to the metal source and both sides need to be coated in turn to create continuous metal film to ensure good encapsulation. In addition, the holder must be constantly rotated to create a uniform metal film.

As is shown in FIG. 10 A-D, 4 devices were compared. In FIG. 10A, no protection was used. In FIG. 10B, a 40 μm parylene-C layer was used as protection. FIG. 10C shows a parylene-C coated bio-compatible silicone. FIG. 10D is the inventive parylene-C-metal-parylene C architecture. Samples are then tested under active soaking conditions.

All tests are performed in saline (0.9 wt % NaCl solution), which is a typical to mimic body fluids. The saline solution is replaced every three days to maintain its constant concentration. In the active soaking tests, different failure mechanisms, as shown in FIG. 11A-D, are observed on samples such as bubbles on parylene, corrosion of metal pads, interface delamination, and corrosion of conductive epoxy which will increase the line resistance and fail the connection. Among them, corrosion of metal pads and conductive epoxy are found to be the major failure modes which can gradually result in the open connection.

Figure 11A:
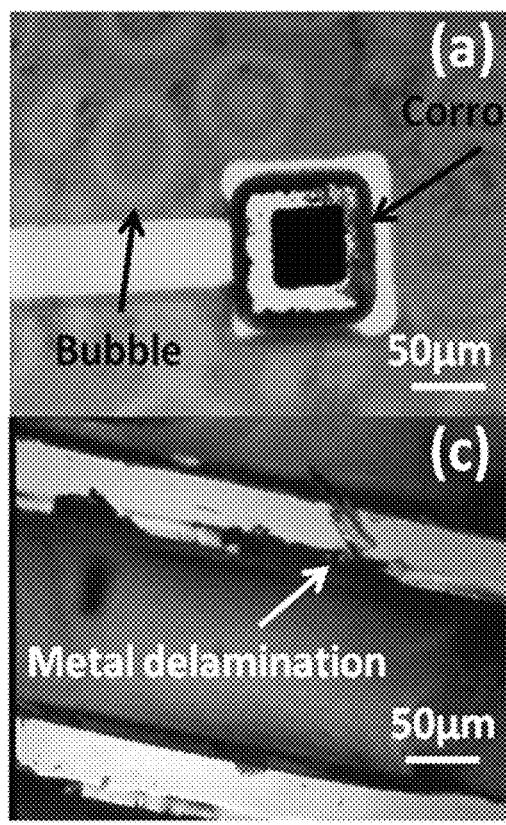
FIGS. 11 A-D show observed failure modes. (A) shows bubbles and corrosion on parylene devices; (B) shows corrosion of sandwiched metals; (C) shows delamination of metal traces on dummy chips; and (D) shows corrosion of conductive epoxy.
Figure 11B:
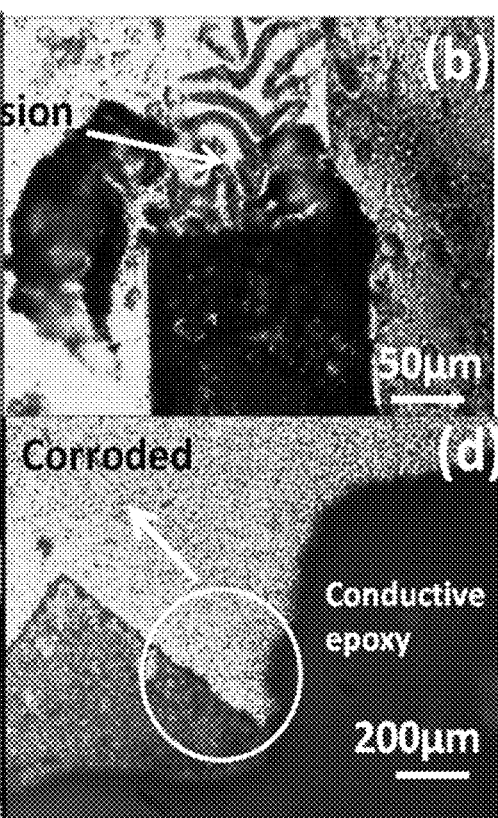
Figure 11C:
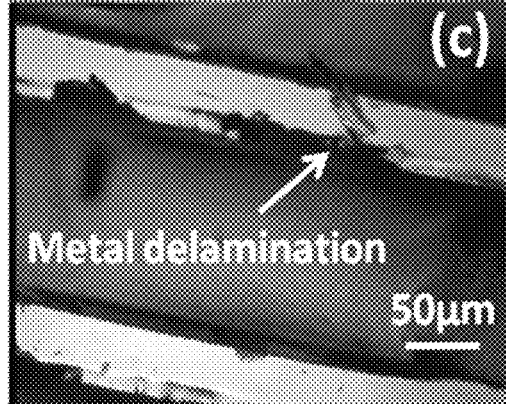
Figure 11D:
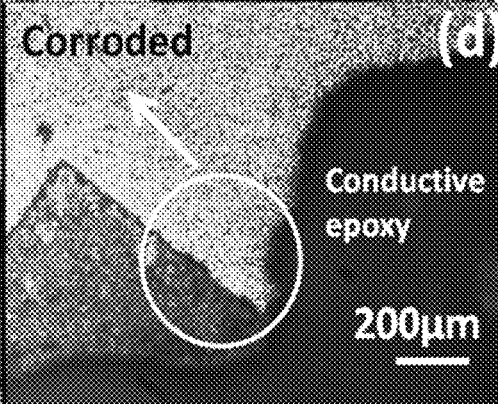

FIG. 11 A-D show observed failure modes, including FIG. 11A which shows bubbles and corrosion, on parylene devices; FIG. 11B shows corrosion of sandwiched metals; FIG. 11C, shows delamination of metal traces on dummy chips; and FIG. 11 D shows corrosion of conductive epoxy after soaking.

For the samples without protection, water vapor can penetrate the thin parylene layer of device itself to damage the metals very quickly, especially under a bias field (see, W. Li et al., *ECS Transactions*, vol. 11, pp. 1-6 (2008)). The corrosion of the metals embedded in parylene is the main reason of failure. For the samples with thick parylene and other protection, uniform bubbles around the whole device are first observed and water vapor gradually diffuses through the protection to attack the device.

Corrosion of conductive epoxy also contributes to the failure in these samples. For some samples with bad parylene coating protection, water vapor can go through very easily. Therefore, failure mechanism is the same as the samples without protection. Samples with better protection (lower WVTR) are observed to have longer lifetime.

Chips with smaller size have longer lifetime under the same protection. Table 1 below shows that the passive components, such as dummy conduction chip and discrete components, under the inventive protection can survive in 97° C. saline solution for more than 44 days. For the active component, amplifier chip, the lifetime is around 37 days. The reason for a shorter lifetime comes from the smaller bonding pads which are easier to be corroded by saline, hence they fail faster.

The approximated Arrhenius relationship (see, J. H. Chang, B. Lu, Y. C. Tai, "Adhesion-enhancement surface treatment for parylene deposition," in Digest Tech. Papers Transducers '11 Conference, Peking, Jun. 5-9, 2011, pp. 378-381) is used here to extrapolate MTTF at body temperature and is expressed as:

$$MTTF \sim A\exp\left(-\frac{Ea}{kT}\right) \quad (2)$$

Where A is the pre-exponential constant; Ea (eV) is the activation energy; and k is the Boltzmann's constant. The failure modes are based on the serious corrosion of metal pads and conductive epoxy. According to the Arrhenius relationship, the lifetime translates to more than 7.5 years, and 6.7 years (a desirable target) for passive and active components of survival period in human body temperature of 37° C. This packaging structure disclosed herein proved to be an acceptable choice for implantable devices.

Table 1 shows the MTTF of various tested samples are recorded and calculated to estimate the lifetime at 37° C. under different protections.

TABLE 1

| Samples | Protection | 97° C. (day) | 85° C. (day) | 60° C. (day) | Ea (eV) | 37° C. | Flexibility |
|---|---|---|---|---|---|---|---|
| Dummy conduction chip | A | 1.6 | 2.5 | 5 | −0.41 | 20 days | YES |
| | B | 17 | 34 | 100+ | −0.66 | 2.5 years | YES |
| | C | 41 | 84 | 100+ | −0.68 | 7.1 years | NO |
| | D | 44 | 90 | 100+ | −0.68 | 7.5 years | YES |
| Commercial amplifier chip | A | 1.5 | 2.4 | 7 | −0.46 | 24 days | YES |
| | B | 15 | 28 | 100+ | −0.59 | 1.5 years | YES |
| | C | 35 | 69 | 100+ | −0.64 | 4.7 years | NO |
| | D | 37 | 78 | 100+ | −0.70 | 6.7 years | YES |
| Discrete components | A | 1.6 | 2.8 | 11 | −0.53 | 41 days | YES |
| | B | 19 | 39 | 100+ | −0.68 | 3.3 years | YES |
| | C | 40 | 83 | 100+ | −0.68 | 6.9 years | NO |
| | D | 46 | 95 | 100+ | −0.69 | 8.1 years | YES |

A: No protection
B: 40 μm PA
C: Silicone + 40 μm PA
D: 20 μm PA + 0.5 μm Metal + 20 μm PA Unexpectedly, the inventive protection scheme "D" was superior with flexibility and a longer life than the other protection schemes.

In another experiment, a device with a glass-protected packaging was soaked in saline, after the power supply was connected, it was determined that water vapor can gradually diffuse through the thick protection barrier. However, it cannot attack the parylene device directly. The failure mode observed is a slow undercut along the interface.

TABLE 2

| Protection | 97° C. (day) | 85° C. (day) | Ea (eV) | 37° C. |
|---|---|---|---|---|
| A | 1.7 | 2.6 | −0.40 | 20 days |
| B | 15 | 31 | −0.69 | 2.7 years |
| C | 40 | 82 | −0.68 | 6.9 years |
| D | 42 | 87 | −0.69 | 7.7 years |
| E | 59 | 107 | −0.68 | 10.3 years |

A: No Protection
B: 40 μm PA
C: 5 mm silicone + 40 μm PA
D: 20 μm PA + 0.5 μm Metal + 20 μm
E: 40 μm PA + 5 mm silicone + glass Table 2 shows the soaking data and lifetime at body temperature. The results indicate that the glass-protected packaging can extend the lifetime to around 10 years. However, "E" is less flexible than "D."

Example 3 Shows a Device that Can be Protected Using the Present Protection Scheme FIGS. 12A-C show one embodiment of a device suitable to be micropackaged using the present invention. In this instance, the present invention provides a retinal implant. In certain aspects, the present invention provides a wireless retinal implant 1200 having a high density multi-channel IC chip, discrete components (caps, inductors, oscillators, and the like), and coils (power and data coils) packaged with a high-density stimulating electrode array. FIGS. 12A-B show the schematic of a retinal implant chip 1205a,b (in A and B) having discrete components 1230a,b and in electrical communication 1207*a,b* with output electronics 1210*a,b*. The chip also has a data coil 1220*a,b* and a power coil 1222*a,b*.

As shown in FIG. 12C, the wireless retinal prosthesis is implanted in a mammalian eye 1240. The chip 1205 and associated components are implanted in the front of the eye (proximal part of the eye) with a cable 1242 leading to the output electrodes 1210*a,b* with an electrode array 1270 implanted in the distal area of the eye. A shown in FIG. 12C, the intraocular RF coil 1245 and the integrated ASICs 1260 are implanted in the front of the eye.

In one aspect, the device to be micropackaged is an integrated circuit (IC) chip. The micropackaged device comprises a substrate such as a thin-film substrate e.g., a parylene substrate.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing a micropackaged device, said method comprising:
 providing a substrate for securing the device;
 coating the device with a first thin-film layer to provide a first thin-film layer over the device;
 depositing a surrounding metal film over the first thin-film layer to produce a metal coat, wherein depositing a surrounding metal film over the first thin-film layer to produce a metal coat is accomplished in a plurality of stages:
 (i) in a first stage, the device is held at about 45° to the metal deposition source to complete encapsulation of one side of the device;
 (ii) in a second stage, the device is flipped 180° and held at about 45° to the metal deposition source to complete encapsulation of the other side of the device; and
 coating the metal coat layer with a second thin-film layer to provide an encapsulated micropackaged device.

2. The method of claim 1, wherein said device is a member selected from the group consisting of an integrated circuit (IC) chip, a printed circuit board (PCB), a microelectromechanical system (MEMS), a capacitor, an inductor, an oscillator, and a combination thereof.

3. The method of claim 1, wherein the first thin-film layer is made of a material selected from the group consisting of parylene, polyimide, Teflon and Kapton.

4. The method of claim 1, wherein the second thin-film layer is made of a material selected from the group consisting of parylene, polyimide, Teflon and Kapton.

5. The method of claim 3, wherein the first thin-film layer is parylene.

6. The method of claim 4, wherein the second thin-film layer is parylene.

7. The method of claim 1, wherein the metal film is a biocompatible metal.

8. The method of claim 7, wherein the metal film is a member selected from the group consisting of Au, Ag, Pt, Pd, Ti and an alloy.

9. The method of claim 1, wherein depositing a surrounding metal film surrounding the device is performed with a holder in constant motion.

10. The method of claim 1, wherein the first thin-film layer, the metal film coating and the second thin-film layer is a sandwich layer.

11. The method of claim 10, wherein said sandwich layer is a parylene-metal film-parylene.

12. The method of claim 10, wherein said sandwich is a corrosion barrier.

13. The method of claim 1, wherein said substrate comprises at least one feedthrough disposed therein to permit at least one input and or at least one output line into said micropackaged device.

14. The micropackaged device produced by the method of claim 1.

* * * * *